US008569258B2

(12) United States Patent
Chatterton

(10) Patent No.: US 8,569,258 B2
(45) Date of Patent: *Oct. 29, 2013

(54) LOW DENSITY LIPOPROTEIN RECEPTOR-MEDIATED SIRNA DELIVERY

(75) Inventor: Jon E. Chatterton, Fort Worth, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,256

(22) Filed: Aug. 13, 2012

(65) Prior Publication Data

US 2012/0315288 A1 Dec. 13, 2012

Related U.S. Application Data

(62) Division of application No. 13/150,317, filed on Jun. 1, 2011, now Pat. No. 8,268,798, which is a division of application No. 12/271,476, filed on Nov. 14, 2008, now abandoned.

(60) Provisional application No. 60/988,162, filed on Nov. 15, 2007.

(51) Int. Cl.
*A61K 48/00* (2006.01)
*C07H 21/02* (2006.01)
*C07H 21/04* (2006.01)
*C07K 5/00* (2006.01)

(52) U.S. Cl.
USPC ........ 514/44; 536/23.1; 536/24.3; 536/24.31; 536/24.5; 536/24.2; 530/300

(58) Field of Classification Search
None
See application file for complete search history.

(56) References Cited

U.S. PATENT DOCUMENTS

| | | | |
|---|---|---|---|
| 5,840,867 A | 11/1998 | Toole et al. | |
| 6,001,648 A | 12/1999 | McCall et al. | |
| 6,207,388 B1 | 3/2001 | Grossman | |
| 6,225,058 B1 | 5/2001 | Munishkin et al. | |
| 6,372,250 B1 | 4/2002 | Pardridge | |
| 6,632,671 B2 | 10/2003 | Unger | |
| 2002/0001810 A1 | 1/2002 | Farrell | |
| 2006/0014172 A1 | 1/2006 | Muller et al. | |
| 2006/0166919 A1 | 7/2006 | Shepard et al. | |
| 2006/0172961 A1 | 8/2006 | Clark et al. | |
| 2006/0172963 A1 | 8/2006 | Shepard et al. | |
| 2006/0172965 A1 | 8/2006 | Shepard et al. | |
| 2006/0223773 A1 | 10/2006 | Clark et al. | |
| 2007/0149473 A1 | 6/2007 | Chatterton et al. | |
| 2007/0155690 A1 | 7/2007 | Chatterton et al. | |

FOREIGN PATENT DOCUMENTS

WO 2007103201 A1 9/2007
WO 2007133812 A1 11/2007

OTHER PUBLICATIONS

Beisiegel, et al.; "Monoclonal antibodies to the low density lipoprotein receptor as probes for study of receptor-mediated endocytosis and the genetics of familial hypercholesterolemia"; The Journal of Biological Chemistry; vol. 256; No. 22; pp. 11923-11931; 1981.
Bora, et al; "complement activation via alternative pathway is critical in the development of laser-induced choroidal neovascularization: role of Factor B and Factor H1"; The Journal of Immunology; vol. 177; pp. 1872-1878; 2006.
Campochiaro; "Potential applications for RNAi to probe pathogenesis and develop new treatments for ocular disorders"; Gene Therapy; vol. 13; pp. 559-562; 2006.
Chu, et al.; "aptamer mediated siRNA delivery"; Nucleic Acids Research; vol. 34, No. 10; e73; p. 1-6; Jun. 1, 2006.
de Knijff, et al.; "Genetic heterogeneity of apolipoprotein E and its influence on plasma lipid and lipoprotein levels"; Human Mutation; vol. 4; pp. 178=194; 1994.
Elbashir, et al. "RNA interference is mediated by 21- and 22-nucleotide RNAs"; Genes and Development; vol. 15; pp. 188-200; 2001.
Fire, et al.; "Potent and specific genetic interference by double-stranded RNA in caenorhabditis elegans"; Letters to Nature; Nature; vol. 391; pp. 808-811 ; Feb. 19, 1998.
Hu-Lieskovan, et al.; "Sequence-specific knockdown of EWS-FLI1 by targeted, nonviral delivery of small interfering RNA inhibits tumor growth in a murine model of metastatic ewing's sarcoma"; Cancer Research; vol. 65; No. 19; pp. 8984-8992; Oct. 1, 2005.
Kim, et al.; "Inhibition of ocular angiogenesis by siRNA targeting vascular endothelial growth factor pathway genes"; American Journal of Pathology; vol. 165; No. 6; pp. 2177-2185; Dec. 2004.
Kumar, et al.; "Transvascular delivery of small interfering RNA to the central nervous system"; Nature; vol. 448; pp. 39-43; Jul. 5, 2007.
Lalazar, et al.; "Site-specific mutagenesis of human apolipoprotein E"; The Journal of Biological Chemistry; vol. 263; No. 8; pp. 3542-3545; 1998.
Nakanjam, et al.; "Synthetic nano-low density lipoprotein as targeted drug delivery vehicle for glioblastoma multiforme"; International Journal of Pharmaceutics; vol. 328; pp. 86-94; 2007.
Pang, et al.; "Preliminary characterization of a transformed cell strain derived from human trabecular meshwork"; Current Eye Research; vol. 13; No. 1; pp. 51-63; 1994.
Qian, et al.; "Targeted drug delivery via the transferrin receptor-mediated endocytosis pathway"; Pharmacological Review; vol. 54; pp. 561-587; 2002.
Reich, et al.; "Small interfering RNA (siRNA) targeting VEGF effectively inhibits ocular neovascularization in a mouse model"; Molecular Vision; vol. 9; pp. 210-216; 2003.
Shen, et al.; "Suppression of ocular neovascularization with siRNA targeting VEGF receptor 1"; Gene Therapy; vol. 13; pp. 225-234; 2006.

(Continued)

*Primary Examiner* — Amy Bowman

(57) ABSTRACT

The invention provides interfering RNA molecule-ligand conjugates useful as a delivery system for delivering interfering RNA molecules to a cell in vitro or in vivo. The conjugates comprise a ligand that can bind to a low density lipoprotein receptor (LDLR) or LDLR family member. Therapeutic uses for the conjugates are also provided.

12 Claims, 5 Drawing Sheets

(56) References Cited

OTHER PUBLICATIONS

Song, et al.; "Antibody mediated in vivo delivery of small interfering RNAs via cell-surface receptors"; Nature Biotechnology; vol. 23; No. 6; pp. 709-711; Jun. 2005.

Spencer, et al.; "Targeted delivery of proteins across the blood-brain barrier"; Proc. Natl. Acad. Sci.; vol. 104; No. 18; pp. 7564-7599; May 1, 2007.

Strickland, et al.; "Diverse roles for the LDL receptor family"; TRENDS in Endocrinology & Metabolism; vol. 13; No. 2; pp. 66-74; Mar. 2002.

Wadia, et al.; "Transducible TAT-HA fusogenic peptide enhances escape of TAT-fusion proteins after lipid raft macropinocytosis"; Nature Medicine; vol. 10; No. 3; pp. 310-315; Mar. 2004.

Rensen, et al.; "Selective targeting of liposomes to macrophasges using a ligland with high affinity for the macrophage scavenger receptor class A"; Curr. Drug. Discov. Tehnol.; vol. 3; pp. 135-144; 2006.

Nakamura et al.; "Octaarginine-modified multifunctional envelope-type nano device for siRNA"; Journal of controlled Release, vol. 119, No. 3, pp. 360-367; May 22, 2007.

Deshpande et al.; "Enhanced cellular uptake of oligonucleotides by EGF receptor-mediated endocytosis in A549 cells"; Pharmaceutical Research; vol. 13, No. 1; pp. 57-61; Jan. 1, 1996.

Fattal et al.,; "Ocular delivery of nucleic acids: antisense oligonucleotides, aptamers and siRNA"; Advanced Drug Delivery Reviews; vol. 58, No. 11; pp. 1203-1223; Nov. 15, 2006.

Search Report for corresponding PCT Application No. US2008083614 dated Sep. 9, 2009.

Grammas et al.; "Thrombin and inflammatory proteins are elevated in Alzheimer's disease microvessels: implications for disease pathogenesis"; Journal of Alzheimer's Disease; vol. 9; pp. 51-58 (2006).

Dot plot Analysis

Histogram Analysis

Overlay Histogram Analysis

LOW DENSITY LIPOPROTEIN RECEPTOR-MEDIATED SIRNA DELIVERY

The present application is a division of U.S. application Ser. No. 13/150,317, filed Jun. 2, 2011 (now allowed), which is a divisional of U.S. patent application Ser. No. 12/271,476, filed Nov. 14, 2008 (now abandoned), which claims the benefit of U.S. Provisional Patent Application Ser. No. 60/988,162 filed on Nov. 15, 2007, the disclosures of which are specifically incorporated by reference herein.

FIELD OF THE INVENTION

The invention relates to interfering RNA delivery conjugates and methods of delivering interfering RNA molecules to a cell via interfering RNA molecule-ligand conjugates, wherein the conjugates comprise an interfering RNA molecule and a ligand that can bind to a low density lipoprotein receptor (LDLR) or LDLR family member. The invention also relates to methods for treating ocular disorders by administering an interfering RNA molecule-ligand conjugate of the invention to a patient in need thereof.

BACKGROUND OF THE INVENTION

RNA interference (RNAi) is a process by which double-stranded RNA (dsRNA) is used to silence gene expression. RNAi is induced by short (i.e. <30 nucleotide) double stranded RNA ("dsRNA") molecules which are present in the cell (Fire et al., 1998, Nature 391:806-811). These short dsRNA molecules called "short interfering RNA" or "siRNA," cause the destruction of messenger RNAs ("mRNAs") which share sequence homology with the siRNA to within one nucleotide resolution (Elbashir et al., 2001, Genes Dev, 15:188-200). It is believed that one strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

RNAi provides a very exciting approach to treating and/or preventing diseases. Some major benefits of RNAi compared with various traditional therapeutic approaches include: the ability of RNAi to target a very particular gene involved in the disease process with high specificity, thereby reducing or eliminating off target effects; RNAi is a normal cellular process leading to a highly specific RNA degradation and a cell-to-cell spreading of its gene silencing effect; and RNAi does not trigger a host immune response as in many antibody based therapies.

Several interfering RNA delivery methods are being tested/developed for in vivo use. For example, siRNAs can be delivered "naked" in saline solution; complexed with polycations, cationic lipids/lipid transfection reagents, or cationic peptides; as components of defined molecular conjugates (e.g., cholesterol-modified siRNA, TAT-DRBD/siRNA complexes); as components of liposomes; and as components of nanoparticles. These approaches have shown varying degrees of success. Thus, there is a need for new and improved methods for delivering siRNA molecules in vivo to achieve and enhance the therapeutic potential of RNAi.

SUMMARY OF THE INVENTION

The invention provides interfering RNA molecule-ligand conjugates, wherein the ligand can bind to a low density lipoprotein receptor (LDLR) or LDLR family member. The invention also provides methods of using the conjugates for delivering an interfering RNA molecule into a cell in vitro or in vivo. In one aspect, an interfering RNA molecule-ligand conjugate of the invention can be used to deliver an interfering RNA molecule to an eye of a patient.

The invention further provides methods of treating or preventing an ocular disorder in a patient, comprising administering to the patient an interfering RNA molecule-ligand conjugate, wherein the ligand can bind to a low density lipoprotein receptor (LDLR) or LDLR family member and wherein the interfering RNA molecule can attenuate expression of a gene associated with the ocular disorder. In certain aspects, the ocular disorder is or is associated with ocular angiogenesis, dry eye, ocular inflammatory conditions, ocular hypertension, or glaucoma. In other aspects, the conjugate is administered by intraocular injection, subconjunctival injection, intravitreal injection, anterior or posterior juxtascleral injection, ocular topical application, intravenous injection, oral administration, intramuscular injection, intraperitoneal injection, transdermal application, intranasal application, or transmucosal application.

Specific preferred embodiments of the invention will become evident from the following more detailed description of certain preferred embodiments and the claims.

DETAILED DESCRIPTION OF THE INVENTION

Figure 1:
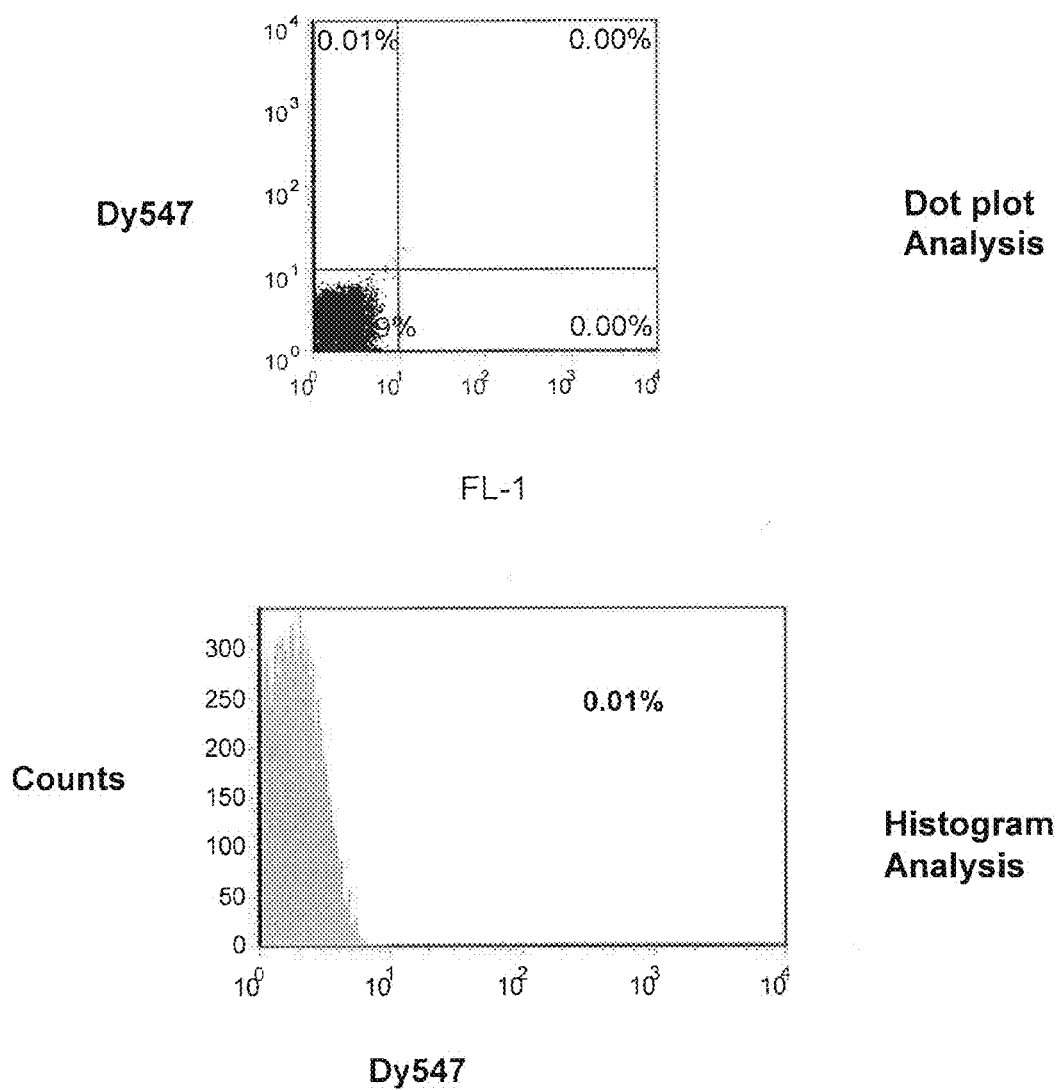
FIG. 1 depicts results of FACS analysis of GTM-3 cells transfected with siGLO siRNA alone. The left upper quadrant of the scatter plots represents the number of cells that have taken up siGLO, Dy547-labeled siRNA. The two dimensional dot plot analysis shows an X-axis for FITC, and a Y-axis for Dy547. The histogram analysis shows cell counts vs. Dy547 fluorescence intensity. The percentages in the histogram and in each quadrant of the dot plot indicate the percentage of Dy547 positive cells.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides interfering RNA delivery conjugates that can deliver interfering RNAs into a cell of a patient. In a particular embodiment, the cell is an eye cell. In yet another embodiment, the conjugates can bind to a low density lipoprotein receptor (LDLR) or LDLR family member on the surface of an eye cell.

The term "receptor" as used herein is intended to encompass the entire receptor or ligand-binding portions thereof. These portions of the receptor particularly include those regions sufficient for specific binding of the ligand to occur.

The ligand of the conjugate can be any molecule that is capable of binding with specificity to an LDL receptor family member, particularly an LDL receptor family member that is expressed on an eye cell. Examples of molecules include, but are not limited to, proteins or aptamers. The term "protein" as used herein includes peptides, polypeptides, consensus molecules, fusion proteins, purified naturally occurring proteins, artificially synthesized proteins, antibodies, and analogs, derivatives or combinations thereof.

The term "aptamer" as used herein refers to nucleic acids (typically DNA, RNA or oligonucleotides) that are capable of binding to a particular molecular target. Aptamers emerge from in vitro selections or other types of aptamer selection procedures well known in the art (e.g. bead-based selection with flow cytometry or high density aptamer arrays) when the nucleic acid is added to mixtures of target molecules. An aptamer is typically between 10 and 300 nucleotides in length. RNA and DNA aptamers can be generated from in vitro selection experiments such as SELEX (Systematic Evolution of Ligands by Exponential Enrichment). Examples of aptamer uses and methods for making/selecting aptamers are described, for example, in Chu et al., 2006, *Nucl. Acids Res.* 34:e73), U.S. Patent Publication No. 20060014172, U.S. Pat. Nos. 5,840,867, 6,001,648, 6225,058, 6,207,388, and U.S. Patent Publication No. 20020001810, the disclosures of all of which are incorporated by reference in their entireties.

Non-limiting examples of LDLR family members include LDLR, very low-density lipoprotein (VLDL) receptor, ApoE receptor, LDL receptor-related protein 1 (LRP-1), LRP-1b, and LRP-2/megalin (see Strickland et al., 2002, *TRENDS in Endocrinol. & Metab.* 13:66-74). A number of ligands that bind to members of the LDLR family of receptors are provided, for example, in Strickland et al., 2002, *TRENDS in Endocrinol. & Metab.* 13:66-74, the disclosure of which is incorporated herein by reference. In some instances, a ligand of an LDLR or LDLR family member may bind to multiple members of the LDLR family. Thus, the term "LDLR ligand" as used herein refers to a ligand that can bind to LDLR and/or one or more members of the LDLR family of receptors.

A particularly preferred ligand family includes peptides comprising the LDLR-binding domain of apolipoprotein B (apoB, Spencer and Verma, 2007, *Proc. Natl. Acad. Sci. USA* 104:7594-7599) or apolipoprotein E (apoE, Lalazar et al., 1988, *J. Biol. Chem.* 263:3542-3545), which are nominal LDL receptor ligands. Three major isoforms of apoE have been identified, including apoE2, apoE3, and apoE4, and numerous apoE variants have been described (see, for example, de Knijff et al., 1994, *Hum. Mutat.* 4:178-194).

The LDLR-binding domain of apoB is

```
                                              SEQ ID NO: 1
    SSVIDALQYKLEGTTRLTRKRGLKLATALSLSNKFVEGS; .
```

An apoE LDLR-binding domain is

```
                                              SEQ ID NO: 2
                EELRVRLASHLRKLRKRLLRDADDLQK; .
```

An interfering RNA molecule can be covalently linked to the apoB or an apoE LDLR-binding domain either directly or via a spacer, such as a glycine spacer of 1, 2, 3, or 4 glycines. Preferably, a glycine spacer is 2 or 3 glycines.

Other examples of ligands that can bind with specificity to LDLR or LDLR family member include antibodies or antibody fragments that can bind LDLR or LDLR family member. These antibodies or antibody fragments are as capable of binding to LDLR or LDLR family member as the nominal receptor ligands. Upon binding of the antibodies to LDLR or LDLR family member on a cell surface, transferal of the antibody and the attached interfering RNA into the cell occurs. The interfering RNA can be attached by any acceptable means for joining the antibody to the interfering RNA such that the interfering RNA can be transferred across the cell membrane in a pharmaceutically active form. In a preferred embodiment, an LDLR-specific antibody or antibody fragment forms a conjugate with the interfering RNA.

In other embodiments, an antibody or antibody fragment that binds to LDLR or an LDLR family member and a second ligand, which is also reactive with the LDLR, are joined together to form a fusion protein. The second ligand can be a second antibody or, more preferably, a nominal ligand such as apoB or apoE, or LDLR binding fragments thereof. Conversely, the two ligands of the fusion protein can be two nominal ligands, or LDLR binding fragments thereof. These fusion proteins have the advantage of possessing the capacity of interacting twice as readily with cells that express LDLR or an LDLR family member, including ocular cells, than conjugates that only have one ligand.

Antibodies that can be used in this invention are reactive with an LDL receptor or LDLR family member on a cell, particularly an eye cell. The term antibody is intended to encompass both polyclonal and monoclonal antibodies. The term antibody is also intended to encompass mixtures of more than one antibody reactive with an LDL receptor or LDLR family member (e.g., a cocktail of different types of monoclonal antibodies reactive with the LDLR), each of which is joined to an interfering RNA to form a conjugate. The term antibody is further intended to encompass whole antibodies, biologically functional fragments thereof, fully humanized antibodies, and chimeric antibodies comprising portions from more than one species, bifunctional antibodies, etc. Biologically functional antibody fragments which can be used are those fragments which can be used for binding of the antibody fragment to the LDLR or LDLR family member to occur. An example of an antibody that binds LDLR and is internalized by the cell is IgG-C7 (Beisiegel et al., 1981, *J. Biol. Chem.* 256:11923-11931).

The interfering RNA can be linked to a ligand using chemical conjugation techniques. In addition to covalent bonding, conjugates can be formed employing non-covalent bonds, such as those formed with bifunctional antibodies, ionic bonds, hydrogen bonds, hydrophobic interactions, etc.

In certain embodiments, an interfering RNA-ligand conjugate of the invention can further comprise a nucleic acid binding protein, such as protamine, covalently linked to the ligand. For example, the ligand of the conjugate can comprise an apoB peptide-protamine fusion protein, an apoE peptide-protamine fusion protein, or an LDLR-specific antibody-protamine fusion protein. Antibody-protamine fusion proteins have been used to deliver siRNA to HIV-infected or envelope-transfected cells (Song et al., 2005, *Nat Biotechnol.* 23:709-717). The interfering RNA molecule can be linked to the ligand via interaction with the nucleic acid binding protein.

In other embodiments, the ligand of the interfering RNA-ligand conjugate of the invention is covalently linked to a polycation, such as polylysine. For example, the conjugate can comprise an apoB or apoE peptide fused to polylysine or another polycation, or an LDLR-specific antibody fused to polylysine or another polycation, such as polyarginine or polyethyleneimine (PEI). Methods for preparing and delivering nucleic acids to a variety of cultured mammalian cells and to tumor-bearing mice using transferrin-polylysine-DNA conjugates have been described (reviewed in Qian, et al., 2002, *Pharmacol Rev* 54:561-587). The interfering RNA molecule can be linked to the ligand via interaction with the polycation.

In certain embodiments, the interfering RNA molecule is linked to the ligand via a peptide consisting entirely of arginines (referred to herein as an "Arg peptide"). Preferably, the Arg peptide comprises 7, 8, 9, 10, or 11 arginines. The Arg peptide can be linked to the C- or N-terminus of a ligand, such as an apoE or apoB peptide LDLR-binding domain, via a glycine spacer of 1 to 4 glycines. Preferably, the glycine spacer is 2 or 3 glycines.

In one embodiment, the Arg peptide is a 9xArg peptide. The term "9xArg peptide" as used herein means a peptide of 9 arginine residues (RRRRRRRRR; SEQ ID NO: 3). In one embodiment, the 9xArg peptide comprises or consists of D-isomers. Negatively charged interfering RNA molecules can bind to the positively charged 9xArg peptide as described in Kumar et al., who recently demonstrated that a 9xArg peptide could be used to link interfering RNA molecules to the C-terminal end of a rabies virus glycoprotein (RVG) targeting peptide for delivery across the blood-brain barrier (Kumar et al., Jun. 17, 2007, *Nature*, epub ahead of print).

In certain embodiments, an interfering RNA-ligand conjugate of the invention is administered to a patient or a cell in the presence of a TAT-HA2 peptide, a ligand-HA2 peptide, or a retro-inverso TAT-HA2 peptide (i.e., the reverse sequence constructed of D-amino acids), which has been shown to enhance release of peptide/protein conjugates from the endosome (Wadia et al., 2004, *Nat. Med.* 10:310). The term "HA2 peptide" means a peptide comprising the N-terminal 20 amino acids of influenza virus hemagglutinin protein. The native HA2 peptide is:

```
                                        SEQ ID NO: 4
         GLFGAIAGFIENGWEGMIDG;.
```

Preferably, the native HA2 peptide comprises L-isomers.

The retro-inverso HA2 peptide is:

```
                                        SEQ ID NO: 5
       GD†I†M†GE†W†GN†E†I†F†GA†I†A†GF†L†G;.
```

D-isomers are denoted by a superscripted dagger (†) to the right of the one-letter code symbol; thus, D† represents D-aspartic acid and L† represents D-leucine.

The presence of HA2 aids release of the interfering RNA delivery system from the endosome into the cytosol, so that the interfering RNA molecule can attenuate expression of a target mRNA in a cell. In certain other embodiments, an HA2 peptide is inserted between the LDLR ligand and the 9xArg, wherein the HA2 peptide is linked to the ligand and 9xArg via glycine spacers. For example, a ligand-HA2 conjugate may comprise the following peptide:

```
                                              SEQ ID NO: 6
    Ligand-GGGD†I†M†GE†W†GN†E†I†F†GA†I†A†GF†L†GGGR†R†
    R†R†R†R†R†R†;.
```

In certain embodiments, the LDLR ligand-9xArg peptide is produced as a single peptide before being conjugated to the interfering RNA molecule. In other embodiments, the LDLR ligand-9xArg peptide can be produced by combining the LDLR ligand and the 9xArg peptide under conditions in which the ligand and the peptide will connect to each other. Such methods for linking two peptides are well known in the art. In yet other embodiments, the 9xArg peptide can be premixed with the interfering RNA molecule and then linked to the LDLR ligand to favor binding of the interfering RNA to the 9xArg end of the peptide. Thus, linkage of the interfering RNA molecule can be accomplished before or after linkage of LDLR ligand with 9xArg.

In certain embodiments, the invention provides a method of attenuating expression of a target mRNA in an eye of a patient, comprising (a) providing an interfering RNA-ligand conjugate, wherein the conjugate binds to a low density lipoprotein receptor (LDLR); and (b) administering the conjugate to an eye of the patient, wherein the interfering RNA molecule can attenuate expression of the target mRNA in the eye.

In certain embodiments, the invention provides a method of preventing or treating an ocular disorder in a patient, the method comprising administering to the patient an interfering RNA-ligand conjugate, wherein the conjugate binds to an LDLR and transports said interfering RNA into an eye cell of the patient.

The term "patient" as used herein means a human or other mammal having an ocular disorder or at risk of having an ocular disorder. Ocular structures associated with such disorders may include the eye, retina, choroid, lens, cornea, trabecular meshwork, iris, optic nerve, optic nerve head, sclera, anterior or posterior segment, or ciliary body, for example. In certain embodiments, a patient has an ocular disorder associated with trabecular meshwork (TM) cells, ciliary epithelium cells, or another cell type of the eye.

The term "ocular disorder" as used herein includes conditions associated with ocular angiogenesis, dry eye, inflammatory conditions, ocular hypertension and ocular diseases associated with elevated intraocular pressure (IOP), such as glaucoma.

The term "ocular angiogenesis," as used herein, includes ocular pre-angiogenic conditions and ocular angiogenic conditions, and includes ocular angiogenesis, ocular neovascularization, retinal edema, diabetic retinopathy, sequela associated with retinal ischemia, posterior segment neovascularization (PSNV), and neovascular glaucoma, for example. The interfering RNAs used in a method of the invention are useful for treating patients with ocular angiogenesis, ocular neovascularization, retinal edema, diabetic retinopathy, sequela associated with retinal ischemia, posterior segment neovascularization (PSNV), and neovascular glaucoma, or patients at risk of developing such conditions, for example. The term "ocular neovascularization" includes age-related macular degeneration, cataract, acute ischemic optic neuropathy (AION), commotio retinae, retinal detachment, retinal tears or holes, iatrogenic retinopathy and other ischemic retinopathies or optic neuropathies, myopia, retinitis pigmentosa, and/or the like.

The term "inflammatory condition," as used herein, includes conditions such as ocular inflammation and allergic conjunctivitis.

The methods of the invention are useful for attenuating expression of particular genes in the eyes of patients using RNA interference.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

In certain embodiments, the invention provides methods of delivering interfering RNA to inhibit the expression of a target mRNA thus decreasing target mRNA levels in patients with ocular disorders.

The phrase "attenuating expression" with reference to a gene or an mRNA as used herein means administering or expressing an amount of interfering RNA (e.g., an siRNA) to reduce translation of a target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Attenuating expression of a target gene by an interfering RNA molecule of the invention can be inferred in a human or other mammal by observing an improvement in symptoms of the ocular disorder.

In one embodiment, a single interfering RNA is delivered to decrease target mRNA levels. In other embodiments, two or more interfering RNAs targeting the mRNA are administered to decrease target mRNA levels. The interfering RNAs may be delivered in the same interfering RNA molecule-ligand conjugate or in separate conjugates.

As used herein, the terms "interfering RNA" and "interfering RNA molecule" refer to all RNA or RNA-like molecules that can interact with RISC and participate in RISC-mediated changes in gene expression. Examples of interfering RNA molecules that can interact with RISC include short hairpin RNAs (shRNAs), single-stranded siRNAs, microRNAs (miRNAs), and dicer-substrate 27-mer duplexes. Examples of "RNA-like" molecules that can interact with RISC include siRNA, single-stranded siRNA, microRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, and dicer-substrate 27-mer duplexes are subsets of "interfering RNAs" or "interfering RNA molecules."

The term "siRNA" as used herein refers to a double-stranded interfering RNA unless otherwise noted. Typically, an siRNA used in a method of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). Typically, an interfering RNA used in a method of the invention has a length of about 19 to 49 nucleotides. The phrase "length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

Single-stranded interfering RNA has been found to effect mRNA silencing, albeit less efficiently than double-stranded RNA. Therefore, embodiments of the present invention also provide for administration of a single-stranded interfering RNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

In certain embodiments, an interfering molecule of the invention comprises at least one of the modifications as described above.

The phrases "target sequence" and "target mRNA" as used herein refer to the mRNA or the portion of the mRNA sequence that can be recognized by an interfering RNA used in a method of the invention, whereby the interfering RNA can silence gene expression as discussed herein. Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Interfering RNA target sequences (e.g., siRNA target sequences) within a target mRNA sequence are selected using available design tools, such as discussed above. Interfering RNAs corresponding to a target sequence are then tested in vitro by transfection of cells expressing the target mRNA followed by assessment of knockdown as described herein. The interfering RNAs can be further evaluated in vivo using animal models as described herein.

The ability of interfering RNA to knock-down the levels of endogenous target gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression. Human corneal epithelial cells or other human ocular cell lines may also be use for an evaluation of the ability of interfering RNA to knock-down levels of an endogenous target gene.

A number of animal models are known that can be used to test the activity of an interfering RNA molecule. For example, siRNA molecules can be tested in murine laser-induced models of choroidal neovascularization (CNV) as described in Reich et al., 2003, *Mol. Vision.* 9:210-216; Shen et al., 2006, *Gene Therapy* 13:225-234; or Bora et al., 2006, *J. Immunol.* 177:1872-1878.

In certain embodiments, an interfering RNA molecule-ligand conjugate comprises an interfering RNA molecule that targets a gene associated with an ocular disorder. Examples of mRNA target genes for which interfering RNAs of the present invention are designed to target include genes associated with the disorders that affect the retina, genes associated with glaucoma, and genes associated with ocular inflammation.

Examples of mRNA target genes associated with the retinal disorders include tyrosine kinase, endothelial (TEK); complement factor B (CFB); hypoxia-inducible factor 1, α subunit (HIF1A); HtrA serine peptidase 1 (HTRA1); platelet-derived growth factor receptor β (PDGFRB); chemokine, CXC motif, receptor 4 (CXCR4); insulin-like growth factor I receptor (IGF1R); angiopoietin 2 (ANGPT2); v-fos FBJ murine osteosarcoma viral oncogene homolog (FOS); cathepsin L1, transcript variant 1 (CTSL1); cathepsin L1, transcript variant 2 (CTSL2); intracellular adhesion molecule 1 (ICAM1); insulin-like growth factor I (IGF1); integrin α5 (ITGA5); integrin β1 (ITGB1); nuclear factor kappa-B, subunit 1 (NFKB1); nuclear factor kappa-B, subunit 2 (NFKB2); chemokine, CXC motif, ligand 12 (CXCL12); tumor necrosis factor-alpha-converting enzyme (TACE); tumor necrosis factor receptor 1 (TNFR1); vascular endothelial growth factor (VEGF); vascular endothelial growth factor receptor 1 (VEGFR1); and kinase insert domain receptor (KDR).

Examples of target genes associated with glaucoma include carbonic anhydrase II (CA2); carbonic anhydrase IV (CA4); carbonic anhydrase XII (CA12); β1 andrenergic receptor (ADBR1); β2 andrenergic receptor (ADBR2); acetylcholinesterase (ACHE); Na+/K+− ATPase; solute carrier family 12 (sodium/potassium/chloride transporters), member 1 (SLC12A1); solute carrier family 12 (sodium/potassium/chloride transporters), member 2 (SLC12A2); connective tissue growth factor (CTGF); serum amyloid A (SAA); secreted frizzled-related protein 1 (sFRP1); gremlin (GREM1); lysyl oxidase (LOX); c-Maf; rho-associated coiled-coil-containing protein kinase 1 (ROCK1); rho-associated coiled-coil-containing protein kinase 2 (ROCK2); plasminogen activator inhibitor 1 (PAI-1); endothelial differentiation, sphingolipid G-protein-coupled receptor, 3 (Edg3 R); myocilin (MYOC); NADPH oxidase 4 (NOX4); Protein Kinase Cδ (PKCδ); Aquaporin 1 (AQP1); Aquaporin 4 (AQP4); members of the complement cascade; ATPase, H+ transporting, lysosomal V1 subunit A (ATP6V1A); gap junction protein α-1 (GJA1); formyl peptide receptor 1 (FPR1); formyl peptide receptor-like 1 (FPRL1); interleukin 8 (IL8); nuclear factor kappa-B, subunit 1 (NFKB1); nuclear factor kappa-B, subunit 2 (NFKB2); presenilin 1 (PSEN1); tumor necrosis factor-alpha-converting enzyme (TACE); transforming growth factor β2 (TGFB2); transient receptor potential cation channel, subfamily V, member 1 (TRPV1); chloride channel 3 (CLCN3); gap junction protein α5 (GJA5); tumor necrosis factor receptor 1 (TNFR1); and chitinase 3-like 2 (CHI3L2).

Examples of mRNA target genes associated with ocular inflammation include tumor necrosis factor receptor superfamily, member 1A (TNFRSF1A); phosphodiesterase 4D, cAMP-specific (PDE4D); histamine receptor H1 (HRH1); spleen tyrosine kinase (SYK); interkeukin 1β (IL1B); nuclear factor kappa-B, subunit 1 (NFKB1); nuclear factor kappa-B, subunit 2 (NFKB2); and tumor necrosis factor-alpha-converting enzyme (TACE).

Such target genes are described, for example, in U.S. patent applications having Publication Nos. 20060166919, 20060172961, 20060172963, 20060172965, 20060223773, 20070149473, and 20070155690, the disclosures of which are incorporated by reference in their entirety.

In other embodiments, the method of delivering an interfering RNA molecule comprises administering to the patient a nanoparticle-ligand conjugate, wherein the interfering RNA molecule is encapsulated in the nanoparticle and the nanoparticle is linked to a ligand that can bind to an LDL receptor (LDLR), which transports the interfering RNA molecule into an eye cell of the patient. Other embodiments of the invention provide a method of preventing or treating an ocular disorder, said method comprising delivering an interfering RNA molecule to the eye of a patient using a nanoparticle-ligand conjugate. Methods for preparing nanoparticles and their use in delivering pharmaceutical agents have been described in U.S. Pat. No. 6,632,671, the disclosures of which are incorporated by reference in their entirety. Methods for preparing nanoparticle-ligand conjugates and their use in delivering pharmaceutical agents have been described in U.S. Pat. No. 6,372,250, the disclosures of which are incorporated by reference in their entirety.

The interfering RNA-ligand conjugates and nanoparticle-ligand conjugates of the invention can be administered by intraocular injection, ocular topical application, intravenous injection, oral administration, intramuscular injection, intraperitoneal injection, transdermal application, or transmucosal application. The form and concentration in which the conjugate is administered (e.g., capsule, tablet, solution, emulsion) will depend at least in part on the route by which it is administered.

In certain embodiments, the method of treating an ocular disease involves an ocular disease associated with TM cells, ciliary epithelium cells, or another cell type of the eye.

In certain embodiments, the invention provides an ocular pharmaceutical composition for preventing or treating an ocular disorder in a patient, comprising an interfering RNA-ligand conjugate or nanoparticle-ligand conjugate of the invention in an ophthalmically acceptable carrier and in a therapeutically effective amount.

Pharmaceutical compositions are formulations that comprise interfering RNAs, or salts thereof, of the invention up to 99% by weight mixed with a physiologically acceptable carrier medium, including those described infra, and such as water, buffer, saline, glycine, hyaluronic acid, mannitol, and the like.

Interfering RNA-ligand conjugates and nanoparticle-ligand conjugates of the present invention are administered as solutions, suspensions, or emulsions. The following are examples of pharmaceutical composition formulations that may be used in the methods of the invention.

|  | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

|  | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

|  | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

|  | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

As used herein, the term "therapeutically effective amount" refers to the amount of interfering RNA or a pharmaceutical composition comprising an interfering RNA determined to produce a therapeutic response in a mammal. Such therapeutically effective amounts are readily ascertained by one of ordinary skill in the art and using methods as described herein.

Generally, a therapeutically effective amount of the interfering RNAs used in a composition of the invention results in an extracellular concentration at the surface of the target cell of from 100 pM to 1 µM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions can be delivered to the surface of the target organ, such as the eye, one to four times per day, or on an extended delivery schedule such as daily, weekly, bi-weekly, monthly, or longer, according to the routine discretion of a skilled clinician. The pH of the formulation is about pH 4.0 to about pH 9.0, or about pH 4.5 to about pH 7.4.

A therapeutically effective amount of a formulation may depend on factors such as the age, race, and sex of the subject, the severity of the ocular disorder, the rate of target gene transcript/protein turnover, the interfering RNA potency, and the interfering RNA stability, for example. In one embodiment, the interfering RNA is delivered topically to a target organ and reaches the target mRNA-containing tissue such as the trabecular meshwork, retina or optic nerve head at a therapeutic dose thereby ameliorating target gene-associated disease process.

Therapeutic treatment of patients with interfering RNAs directed against target mRNAs is expected to be beneficial over small molecule treatments by increasing the duration of action, thereby allowing less frequent dosing and greater patient compliance, and by increasing target specificity, thereby reducing side effects.

An "ophthalmically acceptable carrier" as used herein refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Mirus Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); nanoparticles; or liposomes. Liposomes are formed from standard vesicle-forming lipids and a sterol, such as cholesterol, and may include a targeting molecule such as a monoclonal antibody having binding affinity for cell surface antigens, for example. Further, the liposomes may be PEGylated liposomes.

The interfering RNA-ligand conjugates and nanoparticle-ligand conjugates may be delivered in solution, in suspension, or in bioerodible or non-bioerodible delivery devices.

Interfering RNA-ligand conjugates and nanoparticle-ligand conjugates may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

In certain embodiments, treatment of ocular disorders with interfering RNA molecules is accomplished by administration of an interfering RNA-ligand conjugate or nanoparticle-ligand conjugate directly to the eye. Local administration to the eye is advantageous for a number or reasons, including: the dose can be smaller than for systemic delivery, and there is less chance of the molecules silencing the gene target in tissues other than in the eye.

A number of studies have shown successful and effective in vivo delivery of interfering RNA molecules to the eye. For example, Kim et al. demonstrated that subconjunctival injection and systemic delivery of siRNAs targeting VEGF pathway genes inhibited angiogenesis in a mouse eye (Kim et al., 2004, *Am. J. Pathol.* 165:2177-2185).

In addition, studies have shown that siRNA delivered to the vitreous cavity can diffuse throughout the eye, and is detectable up to five days after injection (Campochiaro, 2006, *Gene Therapy* 13:559-562).

Interfering RNA-ligand conjugates and nanoparticle-ligand conjugates may be delivered directly to the eye by ocular tissue injection such as periocular, conjunctival, sub-tenon, intracameral, intravitreal, intraocular, anterior or posterior juxtascleral, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, interfering RNA-ligand conjugates and nanoparticle-ligand conjugates may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA-ligand conjugate or nanoparticle-ligand conjugate in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA-ligand conjugate or nanoparticle-ligand conjugate is combined with a preservative in an appropriate vehicle, such as mineral oil, liquid lanolin, or white petrolatum. Sterile ophthalmic gel formulations may be prepared by suspending the interfering RNA-ligand conjugate or nanoparticle-ligand conjugate in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

In certain embodiments, the invention also provides a kit that includes reagents for attenuating the expression of an mRNA as cited herein in a cell. The kit contains an interfering RNA molecule-ligand conjugate and/or the necessary components for interfering RNA molecule-ligand conjugate production (e.g., an interfering RNA molecule as well as the ligand and necessary materials for linking). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and a ligand. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

EXAMPLES

The following example, including the experiments conducted and results achieved are provided for illustrative purposes only and are not to be construed as limiting the invention.

Example 1

Delivery of siGLO siRNA to GTM-3 Cells Using 9xArg-Linked Ligand Peptides

The ability of low density lipoprotein receptor (LDLR) ligand peptides to facilitate cellular uptake of siRNA molecules was examined using a fluorescent control siRNA (si- GLO Cyclophilin B; Dharmacon, Lafayette, Colo.) conjugated to a ligand peptide via 9xArg and a glaucomatous trabecular meshwork cell line (GTM-3) as the target cells.

GTM-3 cells (Pang, I. H., et al., 1994 *Curr Eye Res.* 13:51-63) were transfected with siGLO siRNA complexed with 9xArg-linked ligand peptides, complexed with 9xArg alone (i.e. no ligand peptide), or alone (via Dharmafect as discussed below). Ligand peptides were apolipoprotein B (apoB) peptide or rabies virus glycoprotein (RVG) peptide (Kumar, et al. *Nature* 448:39-43, 2007). RVG peptide was used as a negative control, since GTM-3 cells do not express nicotinic acetylcholine receptors, the receptor on neuronal cells to which RVG binds.

The 9xArg, ApoB-9xArg, and RVG-9xArg peptides were purchased from Sigma (St. Louis, Mo.).

```
ApoB-9xArg:
                                           (SEQ ID NO: 7)
SVIDALQYKLEGTTRLTRKRGLKLATALSLSNKFVEGSGGR†R†R†R†
R†R†R†R†R†;

RVG-9xArg:
                                           (SEQ ID NO: 8)
YTIWMPENPRPGTPCDIFTNSRGKRASNGGGGR†R†R†R†R†R†R†R†;
and 9xArg:
                                           (SEQ ID NO: 3)
R†R†R†R†R†R†R†R†R†.
```

A superscripted dagger (†) to the right of the one-letter code symbol denotes the use of a D-amino acid isomer as opposed to the standard L-amino acid isomer.

To generate the siRNA-ligand conjugates, siGLO siRNA was resuspended in 1× siRNA buffer, an aqueous solution of 20 mM KCl, 6 mM HEPES (pH 7.5), 0.2 mM $MgCl_2$, and incubated with ApoB-9xArg, RVG-9xArg, or 9xArg at a 1:10 molar ratio of siRNA to peptide for 30 minutes at room temperature. The siRNA-peptide complexes were applied to GTM-3 cells in serum-free medium at a final siRNA concentration of 100 nM. After 4 hours, the medium was replaced with DMEM supplemented with 10% FBS. After 24 hours, the cells were harvested, and uptake of siGLO siRNA was measured in a LSRII flow cytometry (BD Biosciences, Franklin Lakes, N.J.). GTM-3 cells, transfected with siGLO siRNA using Dharmafect 1 (Dharmacon, Lafayette, Colo.) according to the manufacturer's instructions, served as a positive control.

Figure 2:
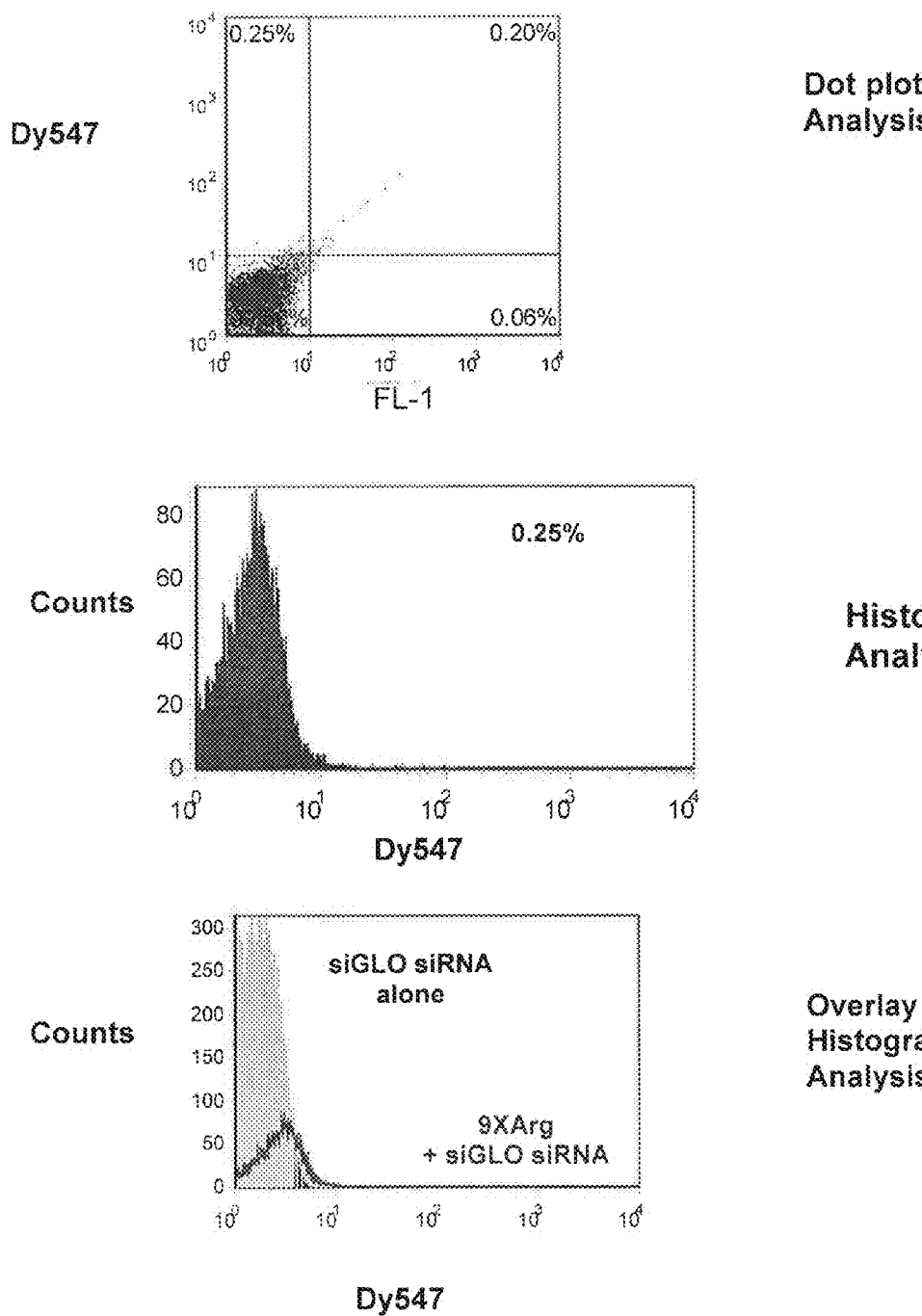
FIG. 2 depicts results of FACS analysis of GTM-3 cells transfected with conjugates of 9XArg peptide+siGLO siRNA. The left upper quadrant of the scatter plots represents the number of cells that have taken up siGLO, Dy547-labeled siRNA. The two dimensional dot plot analysis shows an X-axis for FITC, and a Y-axis for Dy547. The histogram analysis shows cell counts vs. Dy547 fluorescence intensity. The percentages in the histogram and in each quadrant of the dot plot indicate the percentage of Dy547 positive cells. The overlay histogram analysis shows the overlay of siGLO siRNA delivered with a 9xArg-siRNA versus siGLO siRNA alone.
Figure 3:
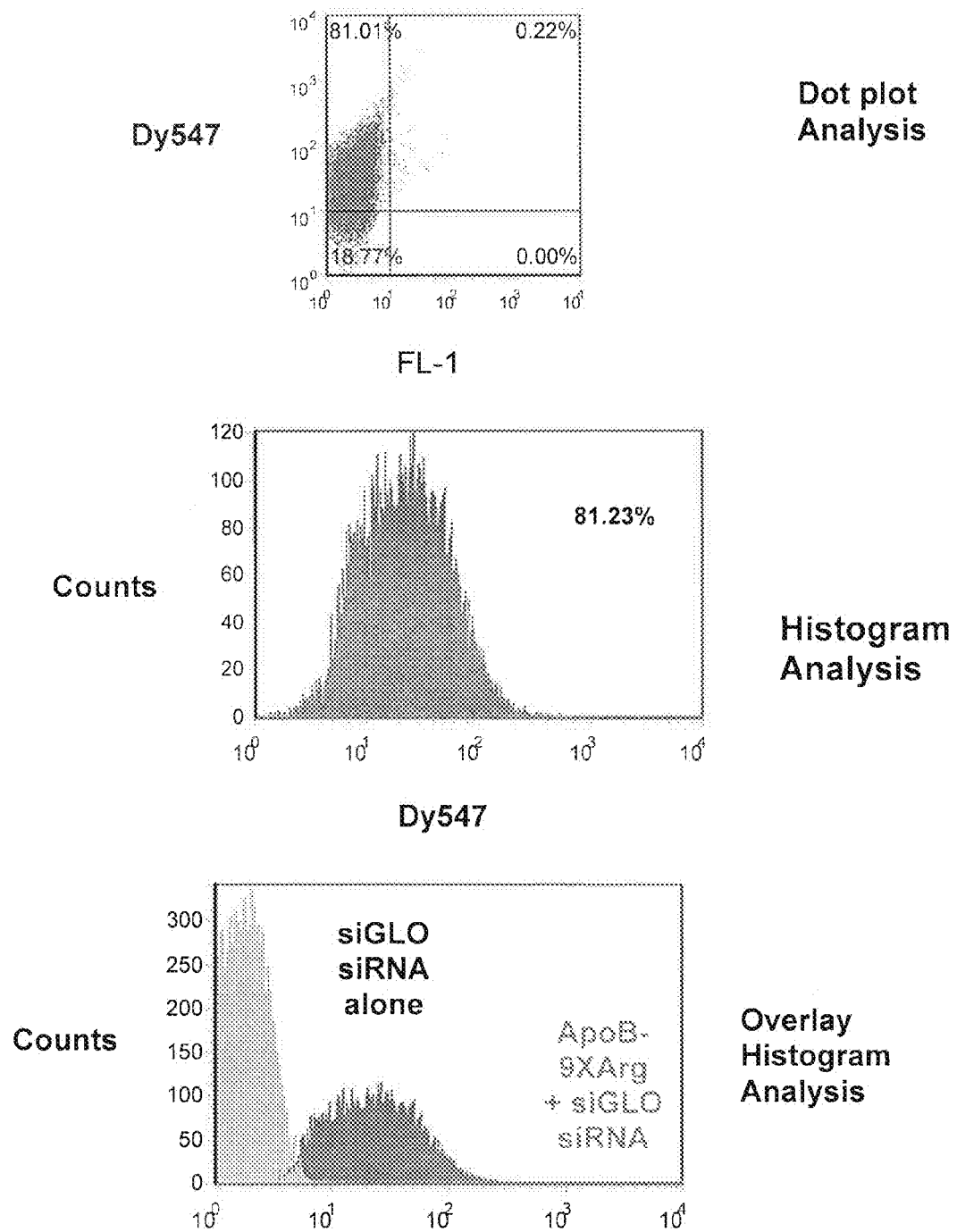
FIG. 3 depicts results of FACS analysis of GTM-3 cells transfected with conjugates of apoB-9XArg peptide+siGLO siRNA. The left upper quadrant of the scatter plots represents the number of cells that have taken up siGLO, Dy547-labeled siRNA. The two dimensional dot plot analysis shows an X-axis for FITC, and a Y-axis for Dy547. The histogram analysis shows cell counts vs. Dy547 fluorescence intensity. The percentages in the histogram and in each quadrant of the dot plot indicate the percentage of Dy547 positive cells. The overlay histogram analysis shows the overlay of siGLO siRNA delivered with a 9xArg-ligand-siRNA conjugate versus siGLO siRNA alone.
Figure 4:
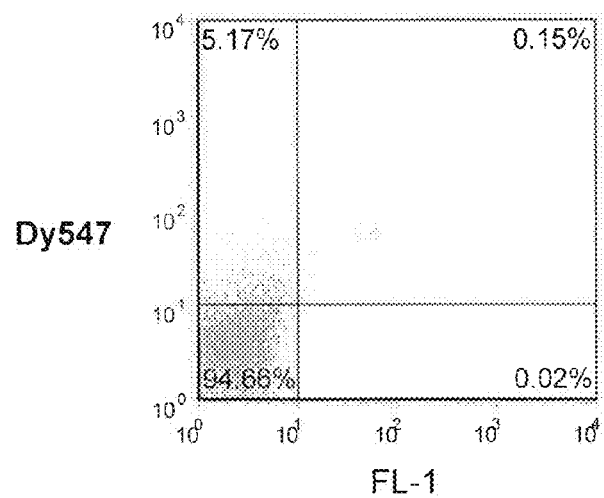
FIG. 4 depicts results of FACS analysis of GTM-3 cells transfected with conjugates of RVG-9XArg peptide+siGLO siRNA. The left upper quadrant of the scatter plots represents the number of cells that have taken up siGLO, Dy547-labeled siRNA. The two dimensional dot plot analysis shows an X-axis for FITC, and a Y-axis for Dy547. The histogram analysis shows cell counts vs. Dy547 fluorescence intensity. The percentages in the histogram and in each quadrant of the dot plot indicate the percentage of Dy547 positive cells. The overlay histogram analysis shows the overlay of siGLO siRNA delivered with a 9xArg-ligand-siRNA conjugate versus siGLO siRNA alone.
Figure 4:
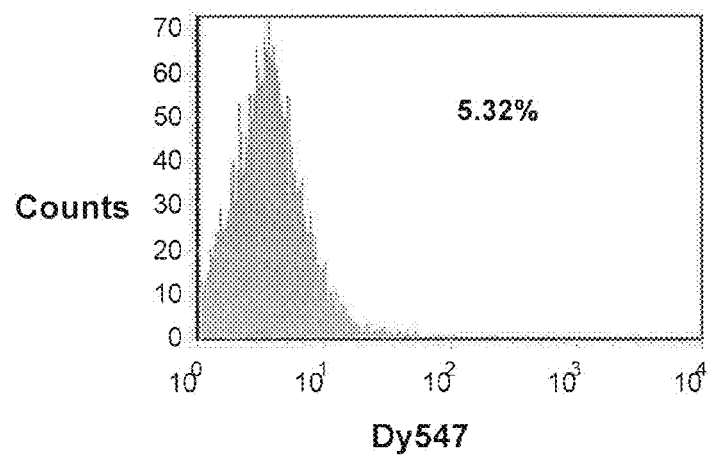
Figure 4:
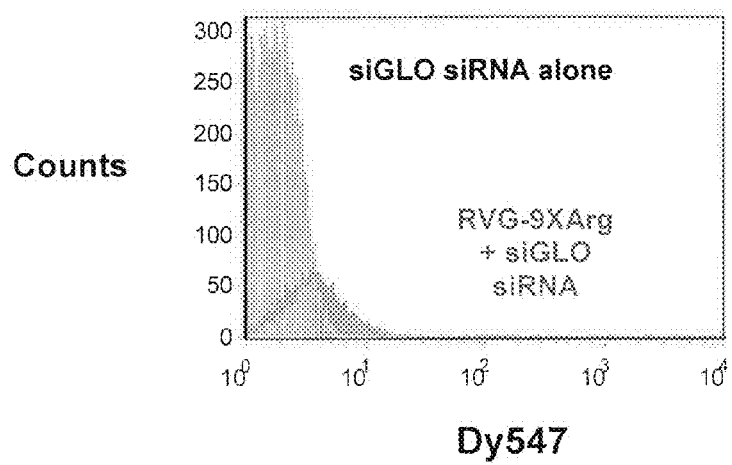
Figure 5:
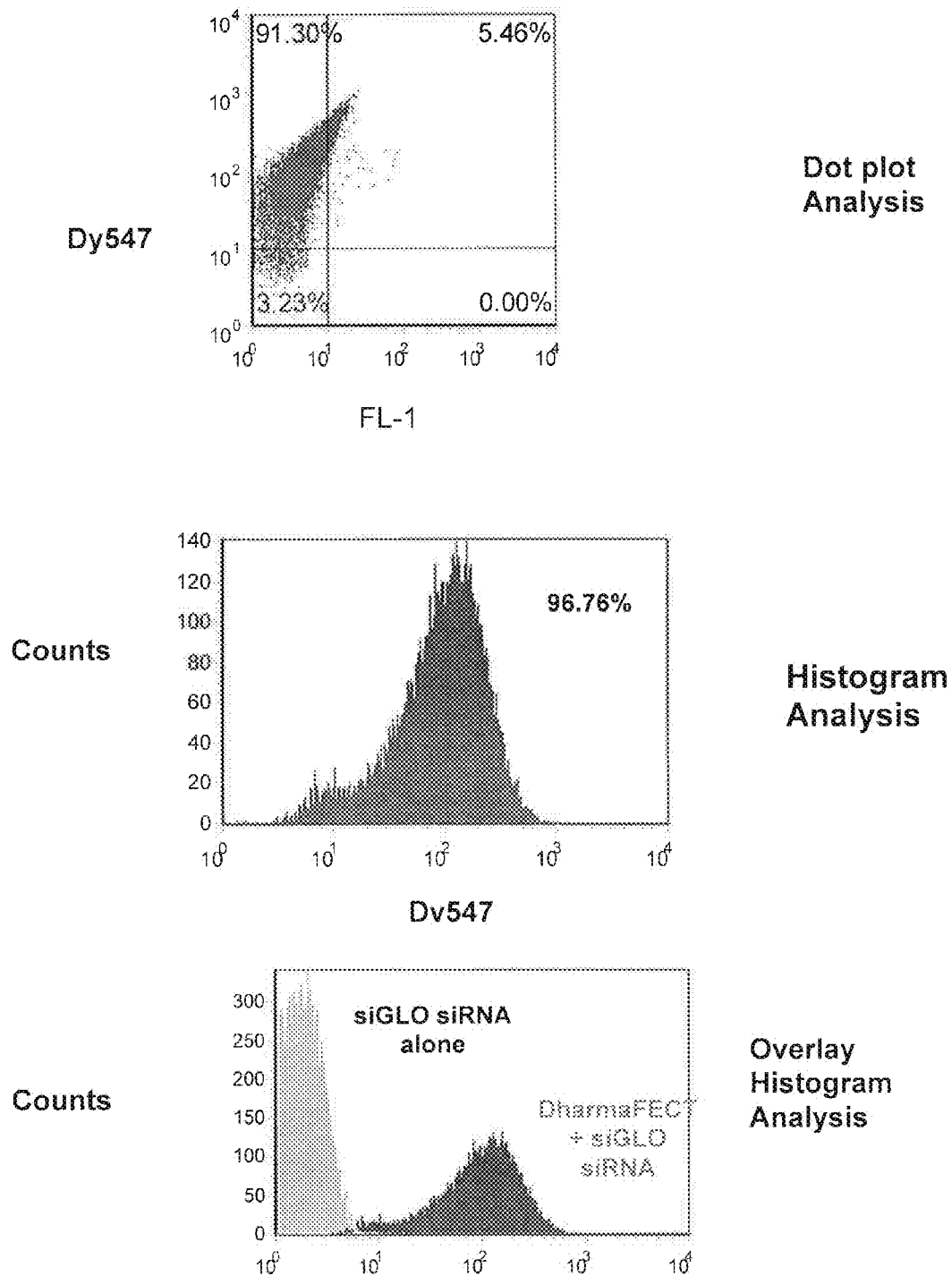
FIG. 5 depicts results of FACS analysis of GTM-3 cells transfected with siGLO siRNA using DharmaFect. The left upper quadrant of the scatter plots represents the number of cells that have taken up siGLO, Dy547-labeled siRNA. The two dimensional dot plot analysis shows an X-axis for FITC, and a Y-axis for Dy547. The histogram analysis shows cell counts vs. Dy547 fluorescence intensity. The percentages in the histogram and in each quadrant of the dot plot indicate the percentage of Dy547 positive cells. The overlay histogram analysis shows the overlay of siGLO siRNA delivered with a DharmaFECT transfected siRNA versus siGLO siRNA alone.

As shown in FIG. 1, GTM-3 cells did not take up siGLO siRNA in the absence of a transfection reagent. Addition of the 9xArg peptide, which lacks a receptor ligand, to the siGLO siRNA did not enhance uptake (FIG. 2). As expected, the RVG-9xArg peptide had little effect on siRNA uptake since GTM-3 cells do not express the receptor for this ligand (FIG. 4). In contrast, the apoB-9xArg peptide enhanced uptake of the siGLO siRNA significantly, causing an increased fluorescence signal in approximately 80% of the cells (FIG. 3). For comparison, lipid-mediated transfection using Dharmafect 1 caused an increased fluorescence signal in over 95% of the cells (FIG. 5).

These results demonstrated that linkage of siRNAs to LDLR ligand peptides can facilitate siRNA delivery to cultured cells.

It should be understood that the foregoing disclosure emphasizes certain specific embodiments of the invention and that all modifications or alternatives equivalent thereto are within the spirit and scope of the invention as set forth in the appended claims.

What is claimed is:

1. A method of delivering an interfering RNA molecule to an eye of a patient, comprising administering to an eye of the patient an interfering RNA delivery conjugate comprising an interfering RNA molecule, a ligand that comprises the LDLR biding domain of apolipoprotein E (apoE), and an HA2 peptide.

2. The method of claim 1, wherein the ligand comprises the LDLR binding domain of apolipoprotein B (apoB).

3. The method of claim 1, wherein the ligand comprises an LDLR-specific antibody or a fragment thereof.

4. The method of claim 1, wherein the interfering RNA molecule is linked to the ligand via a nucleic acid binding protein.

5. The method of claim 1, wherein the interfering RNA molecule is linked to the ligand via a polycation.

6. The method of claim 5, wherein the polycation is polylysine.

7. The method of claim 1, wherein the interfering RNA molecule is linked to the ligand via a 7×Arg peptide, 8×Arg peptide, 9×Arg peptide, 10×Arg peptide, or 11×Arg peptide.

8. The method of claim 7, wherein the interfering RNA molecule is linked to the ligand via a 9×Arg peptide.

9. The method of claim 1, wherein the interfering RNA molecule is a siRNA, miRNA, or shRNA.

10. The method of claim 1, wherein the interfering RNA molecule is covalently linked to the ligand.

11. The method of claim 1, wherein the interfering RNA delivery conjugate is administered by intraocular injection, subconjunctival injection, intravitreal injection, or anterior or posterior juxtascleral injection.

12. The method of claim 1, wherein the patient has ocular angiogenesis, dry eye, an ocular inflammatory condition, ocular hypertension, or glaucoma.

* * * * *

SEQUENCE LISTING

```
<160> NUMBER OF SEQ ID NOS: 8

<210> SEQ ID NO 1
<211> LENGTH: 39
<212> TYPE: PRT
<213> ORGANISM: Homo sapiens

<400> SEQUENCE: 1

Ser Ser Val Ile Asp Ala Leu Gln Tyr Lys Leu Glu Gly Thr Thr Arg
1               5                   10                  15

Leu Thr Arg Lys Arg Gly Leu Lys Leu Ala Thr Ala Leu Ser Leu Ser
            20                  25                  30

Asn Lys Phe Val Glu Gly Ser
        35

<210> SEQ ID NO 2
<211> LENGTH: 27
<212> TYPE: PRT
<213> ORGANISM: Homo sapiens

<400> SEQUENCE: 2

Glu Glu Leu Arg Val Arg Leu Ala Ser His Leu Arg Lys Leu Arg Lys
1               5                   10                  15

Arg Leu Leu Arg Asp Ala Asp Asp Leu Gln Lys
            20                  25

<210> SEQ ID NO 3
```

```
<211> LENGTH: 9
<212> TYPE: PRT
<213> ORGANISM: Artificial
<220> FEATURE:
<223> OTHER INFORMATION: synthetic peptide

<400> SEQUENCE: 3

Arg Arg Arg Arg Arg Arg Arg Arg
1               5

<210> SEQ ID NO 4
<211> LENGTH: 20
<212> TYPE: PRT
<213> ORGANISM: Influenza virus

<400> SEQUENCE: 4

Gly Leu Phe Gly Ala Ile Ala Gly Phe Ile Glu Asn Gly Trp Glu Gly
1               5                   10                  15

Met Ile Asp Gly
            20

<210> SEQ ID NO 5
<211> LENGTH: 20
<212> TYPE: PRT
<213> ORGANISM: Artificial
<220> FEATURE:
<223> OTHER INFORMATION: synthetic pepitde

<400> SEQUENCE: 5

Gly Asp Ile Met Gly Glu Trp Gly Asn Glu Ile Phe Gly Ala Ile Ala
1               5                   10                  15

Gly Phe Leu Gly
            20

<210> SEQ ID NO 6
<211> LENGTH: 33
<212> TYPE: PRT
<213> ORGANISM: Artificial
<220> FEATURE:
<223> OTHER INFORMATION: synthetic peptide

<400> SEQUENCE: 6

Gly Gly Gly Asp Ile Met Gly Glu Trp Gly Asn Glu Ile Phe Gly Ala
1               5                   10                  15

Ile Ala Gly Phe Leu Gly Gly Gly Arg Arg Arg Arg Arg Arg Arg Arg
            20                  25                  30

Arg

<210> SEQ ID NO 7
<211> LENGTH: 49
<212> TYPE: PRT
<213> ORGANISM: Artificial
<220> FEATURE:
<223> OTHER INFORMATION: synthetic peptide

<400> SEQUENCE: 7

Ser Val Ile Asp Ala Leu Gln Tyr Lys Leu Gly Thr Thr Arg Leu
1               5                   10                  15

Thr Arg Lys Arg Gly Leu Lys Leu Ala Thr Ala Leu Ser Leu Ser Asn
            20                  25                  30

Lys Phe Val Glu Gly Ser Gly Gly Arg Arg Arg Arg Arg Arg Arg Arg
        35                  40                  45

Arg
```

```
<210> SEQ ID NO 8
<211> LENGTH: 41
<212> TYPE: PRT
<213> ORGANISM: Artificial
<220> FEATURE:
<223> OTHER INFORMATION: synthetic peptide

<400> SEQUENCE: 8

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
            35                  40
```